United States Patent
Mallya et al.

(10) Patent No.: US 9,336,591 B2
(45) Date of Patent: May 10, 2016

(54) INTEGRATION OF USER INPUTS AND CORRECTION OF DEFORMATION VECTOR FIELD IN DEFORMABLE IMAGE REGISTRATION WORKFLOW

(75) Inventors: Yogisha Mallya, Bangalore (IN); Karl Antonin Bzdusek, Madison, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 324 days.

(21) Appl. No.: 14/237,910

(22) PCT Filed: Aug. 16, 2012

(86) PCT No.: PCT/IB2012/054169
§ 371 (c)(1),
(2), (4) Date: Feb. 10, 2014

(87) PCT Pub. No.: WO2013/030707
PCT Pub. Date: Mar. 7, 2013

(65) Prior Publication Data
US 2014/0201670 A1 Jul. 17, 2014

Related U.S. Application Data

(60) Provisional application No. 61/528,790, filed on Aug. 30, 2011.

(51) Int. Cl.
*G06K 9/00* (2006.01)
*G06T 7/00* (2006.01)
(Continued)

(52) U.S. Cl.
CPC ............. *G06T 7/0012* (2013.01); *A61N 5/103* (2013.01); *G06F 3/0481* (2013.01);
(Continued)

(58) Field of Classification Search
USPC ......... 382/100, 103, 106–107, 128–134, 154, 382/162, 168, 173, 181, 199, 232, 254–255, 382/274, 276, 285–291, 305, 312, 256; 375/7.084; 378/4, 21, 16; 345/424
See application file for complete search history.

(56) References Cited

U.S. PATENT DOCUMENTS

| | | | | |
|---|---|---|---|---|
| 5,633,951 A | * | 5/1997 | Moshfeghi | G06K 9/6207 375/E7.084 |
| 7,352,370 B2 | * | 4/2008 | Wang | A61N 5/103 345/424 |

(Continued)

FOREIGN PATENT DOCUMENTS

| WO | 2007014092 A2 | 2/2007 |
|---|---|---|
| WO | 2007014105 A2 | 2/2007 |

(Continued)

OTHER PUBLICATIONS

Erem, B., et al.; Interactive Deformable Registration Visualization and Analysis of 4D Computed Tomography; 2008; Medical Biometrics-Lecture Notes in Computer Science; Springer; pp. 232-239.

(Continued)

*Primary Examiner* — Seyed Azarian (57) ABSTRACT

A deformation vector field (DVF) (22) is computed that relatively spatially registers a first image (16) and a second image (14). A contour (26) delineating a structure in the first image is adapted using the DVF to generate an initial contour (52) for the structure in the second image. A final contour (56) is received for the structure in the second image. The DVF is corrected based on the initial and final contours for the structure in the second image to generate a corrected DVF (32). The correction may comprise computing an adjustment DVF (62) relating the initial and final contours and combining the DVF and the adjustment DVF to generate the corrected DVF. The final contour may be received by displaying the second image overlaid with the initial contour, and receiving user adjustments of the overlaid contour with the overlaid contour updated for each received user adjustment.

17 Claims, 5 Drawing Sheets

(51) Int. Cl.
*A61N 5/10* (2006.01)
*G06F 3/0481* (2013.01)
*G06F 3/0484* (2013.01)
*A61B 6/00* (2006.01)

(52) U.S. Cl.
CPC ......... *G06F 3/04845* (2013.01); *G06T 7/0024* (2013.01); *G06T 2200/24* (2013.01); *G06T 2207/10081* (2013.01); *G06T 2207/10088* (2013.01); *G06T 2207/10104* (2013.01); *G06T 2207/10108* (2013.01); *G06T 2207/20012* (2013.01); *G06T 2207/20104* (2013.01); *G06T 2207/30096* (2013.01)

(56) References Cited

U.S. PATENT DOCUMENTS

| 7,945,117 | B2* | 5/2011 | Hermosillo Valadez | ............... G06K 9/6206 382/128 |
|---|---|---|---|---|
| 2007/0116381 | A1* | 5/2007 | Khamene | ............. G06K 9/6206 382/276 |
| 2009/0190809 | A1 | 7/2009 | Han et al. | |
| 2010/0232572 | A1 | 9/2010 | Nord et al. | |
| 2013/0004034 | A1* | 1/2013 | Tome | .................... G06T 7/0024 382/128 |
| 2013/0259335 | A1 | 10/2013 | Mallya et al. | |

FOREIGN PATENT DOCUMENTS

| WO | 2010086776 | A1 | 8/2010 |
| WO | 2010148250 | A2 | 12/2010 |

OTHER PUBLICATIONS

Muyan-Ozcelik, P., et al.; Fast Deformable Registration on the GPU: A CUDA Implementation of Demons; 2008; IEEE Trans. on Int'l. Conf. on Computational Sciences and Its Applications (ICCSA); pp. 223-233.

* cited by examiner

INTEGRATION OF USER INPUTS AND CORRECTION OF DEFORMATION VECTOR FIELD IN DEFORMABLE IMAGE REGISTRATION WORKFLOW

The following relates to the medical imaging arts. It particularly relates to image registration of successive images acquired in conjunction with the performance of fractionated radiation therapy, and is described with particular reference thereto. The following is more generally related to registration of images with previously acquired and segmented images generally.

In fractionated radiation therapy, the radiation dose is spread out over a series of radiation therapy sessions. Fractionation of the radiation dose provides certain benefits such as allowing the patient to recover in between sessions, and enabling medical personnel to assess the effectiveness of the radiation therapy from session to session, and to make adjustments, for example to accommodate a reduction in size over time of the malignant tumor (perhaps due to effectiveness of the radiation therapy).

In intensity modulated radiation therapy (IMRT), the radiation beam is controlled to deliver the radiation dose to the malignant tissue while limiting the radiation exposure of surrounding healthy tissue, especially so-called "critical" organs that may be especially susceptible to radiation damage. IMRT can employ various radiation beam modulation tools such as multi-leaf collimator (MLC) apparatus, a tomographically orbiting radiation source providing irradiation over a large angular range (up to 360°), and so forth.

However, a difficulty in fractionated radiation therapy is that the locations, sizes, orientations, and other aspects of the tumor and surrounding organs or tissue may change over time due to numerous factors such as weight loss or gain, natural movement of organs within the body, and so forth. If these changes are not accommodated, then the IMRT parameters may result in irradiation that is not well targeted to the malignant tumor and instead partially overlaps and irradiates critical structures.

To accommodate changes over time, it is known to acquire an initial planning image, which is typically of high resolution, followed by subsequent acquisition of so-called "treatment" images which are acquired, for example, between radiation therapy sessions. The treatment images may be of lower resolution, and may also be of a different modality than the planning image. For example, the planning image may be a high resolution computed tomography (CT) image while subsequent treatment images may be lower resolution CT images (possibly acquired using a CT scanner integrated with the radiation therapy system) and/or emission images such as positron emission tomography (PET) or single photon emission computed tomography (SPECT) images. Emission images such as PET or SPECT images advantageously tend to provide functional information and can identify necrotic tissue, tissue having a high density of microvasculature, or so forth.

In a typical fractionated IMRT process, the initial planning image is manually or semi-automatically segmented to delineate the malignant tumor that is to be the target of the irradiation, and any surrounding critical structures whose irradiation should be limited. These features are delineated by contours. The planning image is also used to generate radiation attenuation map. In the case of a CT planning image, this entails adjusting the CT image, which is essentially an attenuation map for the x-rays used in the CT imaging, to account for the difference in energy of the radiation therapy beam.

Thereafter, to account for change over time, a treatment image is acquired. The treatment image and the planning image are spatially registered. For IMRT non-rigid spatial registration is typically employed in order to precisely account for changes more complex than simple rigid translation or rotation. The tumor and critical structures are contoured in the treatment image and the resulting contours are compared with the contours of the planning image so as to identify any changes.

The contouring process is manually intensive and potentially prone to human error. Contouring can be partially automated by adapting the planning image contours to the treatment image based on the non-rigid registration deformation vector field (DVF). However, the resulting contours are sometimes not sufficiently accurate, and may require manual correction. Furthermore, the contours are usually not propagated to all aspects of the radiation therapy planning For example, the contours are typically not used for correcting the radiation attenuation map, or for computing dose accumulation, or so forth.

The following contemplates improved apparatuses and methods that overcome the aforementioned limitations and others.

According to one aspect, a method comprises: computing a deformation vector field (DVF) relatively spatially registering first and second images; adapting a contour delineating a structure in the first image using the DVF to generate an initial contour for the structure in the second image; receiving a final contour for the structure in the second image; and correcting the DVF based on the initial and final contours for the structure in the second image to generate a corrected DVF; wherein the computing, adapting, and correcting are performed by an electronic processing device. In some embodiments the correction comprises computing an adjustment DVF relating the initial and final contours and combining the DVF and the adjustment DVF to generate the corrected DVF.

According to another aspect, a non-transitory storage medium stores instructions executable by an electronic processing device to perform a method comprising: adjusting a contour of a second image; and updating a deformation vector field (DVF) mapping between the second image and a first image based on the adjustment of the contour to generate an updated DVF mapping between the second image and the first image.

According to another aspect, an apparatus comprises: an electronic processing device configured to compute a deformation vector field (DVF) spatially mapping a first image and a second image; and a user interface configured to display the second image and an overlaid contour comprising an initial contour generated by mapping a contour of the first image to the second image using the DVF. The user interface is further configured to receive and display user adjustments of the overlaid contour wherein the overlaid contour adjusted by said user adjustments defines a final contour. The electronic processing device is further configured to correct the DVF based on the initial contour and the final contour to generate a corrected DVF. In some embodiments the first image is a planning image for planning intensity-modulated radiation therapy (IMRT) and the second image is a treatment image for updating the IMRT, and the electronic processing device is further configured to update one or more parameters of the IMRT based at least on the corrected DVF. In some such embodiments the apparatus further includes an IMRT delivery system configured to perform a session of the IMRT using the one or more updated parameters.

One advantage resides in providing automated feedback from manual contour correction back to the non-rigid spatial image registration, so that processing reliant upon accuracy of the image registration benefits from the manual contour correction.

Another advantage resides in providing more accurate fractionated radiation therapy by feeding contour corrections back to the non-rigid spatial registration of treatment and planning images.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

Figure 1:
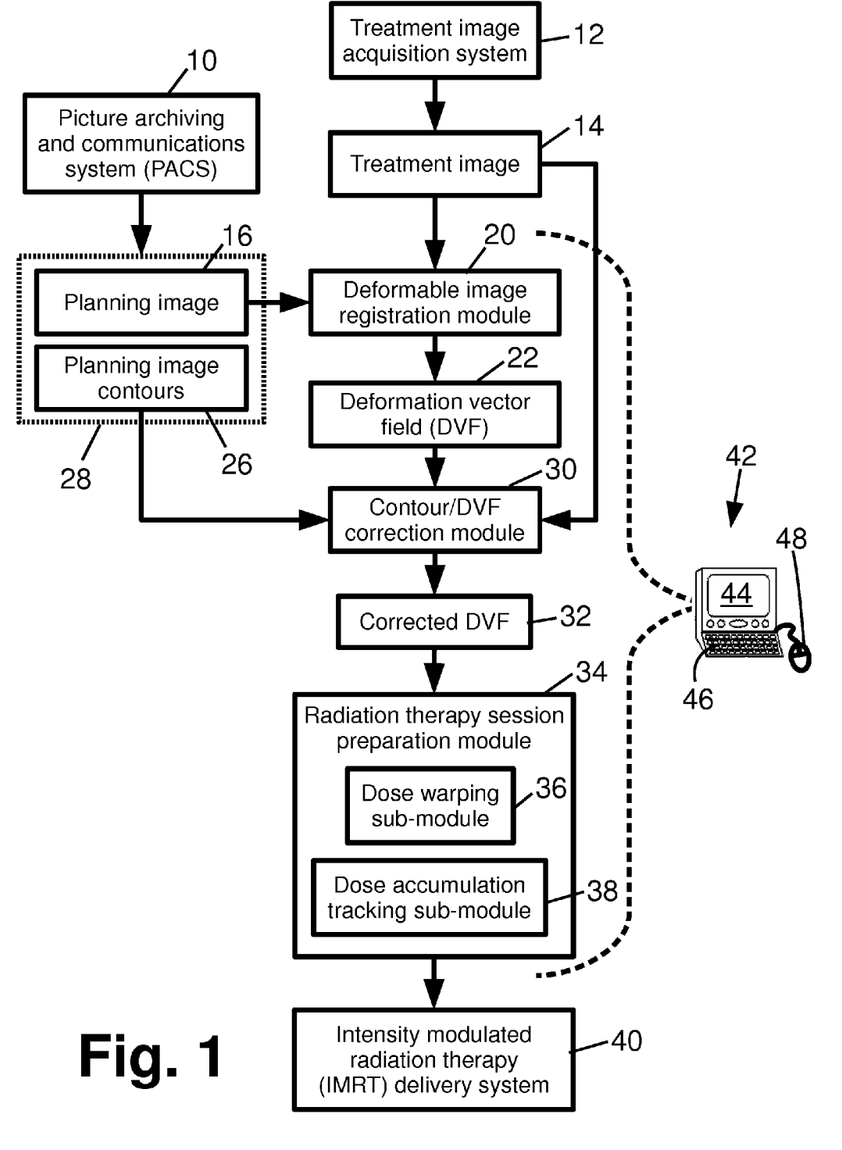
FIG. 1 diagrammatically shows a fractionated intensity modulated radiation therapy (IMRT) system as disclosed herein.

With reference to FIG. 1, an illustrative intensity-modulated radiation therapy (IMRT) system is described. The intensity-modulated radiation therapy is performed as a fractionated radiation therapy, that is, over a series of radiation therapy sessions. Prior to commencement of the radiation therapy, a planning image is acquired of the subject (e.g. oncology patient, animal undergoing veterinary radiation therapy, or so forth). The planning image is typically a transmission computed tomography (CT) image, although the planning image may be acquired by another imaging modality such as magnetic resonance (MR), an emission modality such as positron emission tomography (PET) or single photon emission computed tomography (SPECT), or so forth. Moreover, it is to be understood that the planning imaging may entail acquiring a volumetric (3D) image, a stack of planar (2D) images collectively defining a volumetric image, or so forth, and moreover the planning imaging may employ two or more different imaging modalities. As an example of the latter case, in some radiation therapy workflows the planning imaging may be performed using (i) CT to acquire anatomical information and (ii) an emission modality such as PET or SPECT to acquire functional information. In some medical institutions, the planning images are stored in a picture archiving and communications system (PACS) 10 from which the planning images may be accessed by authorized medical personnel such as an oncologist, radiologist, the patient's personal physician, or so forth.

The planning images are typically analyzed by an oncologist or other qualified medical personnel in order to plan the radiation therapy regimen. In a typical planning process, the oncologist or other qualified medical personnel manually draw contours on or in one or more the planning images. These contours delineate the malignant tumor (or, more generally, malignant tissue that is to be the target of the radiation therapy) and typically also delineate one or more "critical" structures, which are organs, tissue, or so forth that is susceptible to substantial damage from radiation exposure. Typically, the goal of the IMRT is to deliver at least a specified radiation dosage to the target tumor or tissue while keeping the radiation exposure of critical structures below a specified maximum allowable level. These contours are stored with the planning image in the PACS 10.

The radiation therapy planning is based on information such as: the contours delineating the tumor and critical structures; radiation dosage thresholds for the tumor (usually a minimum dosage threshold) and for critical structures (usually a maximum allowable exposure); and a radiation attenuation map for the subject. The latter is typically generated from the planning image. For example, if the planning image is a CT image then the attenuation map can be generated by adjusting the attenuation values of the CT image to account for the difference in photon energy between the x-ray radiation used in the CT imaging and the radiation used in the radiation therapy. These various inputs are used to determine a set of parameters for operating the radiation therapy delivery system during a radiation therapy session. The parameters may include multi-leaf collimator (MLC) apparatus settings, rotation speed and/or trajectory of a tomographic radiation source, total beam power, and so forth. Settings or other values for the various parameters of the radiation therapy delivery system that satisfy the dosage thresholds for the tumor and critical organs are determined for each radiation therapy session of the fractionated IMRT using an automated (or "inverse") planning procedure.

The planning process can take a relatively long time. The planning images are typically acquired with high resolution, and contouring may be performed in each slice of a stack of slices in order to delineate the tumor and critical structures three-dimensionally. For a complex radiation therapy delivery system including hundreds or thousands of MLC elements and/or a tomographic (360°) set of views around the subject, the inverse planning, although performed by a computer or other electronic processing device, is complex and can take a substantial amount of computing time. As a consequence, the planning images are typically acquired some time (e.g., hours, days, or longer) before commencement of the first radiation therapy session. During this interval, changes may occur, such as organ movement due to expansion, contraction, formation, or dissolution of air pockets in the subject, changes in patient weight, growth or shrinkage of the malignant tumor, or so forth.

Accordingly, with continued reference to FIG. 1, a treatment image acquisition system 12 is employed to acquire a treatment image 14 of the subject a short time prior to commencement of the radiation therapy session. The treatment image acquisition system 12 is typically a CT imaging scanner, although an MR or another imaging modality is also contemplated. To assess changes that have occurred since the radiation therapy planning was performed, the treatment image 14 is spatially registered with a corresponding planning image 16 retrieved from the PACS 10.

In the illustrative embodiment, the spatial registration is performed by a deformable image registration module 20 using a deformable image registration algorithm such as the Demons deformable registration technique or another deformable image registration technique such as level sets, B-spline, or so forth. The output of the deformable image registration is a deformation vector field (DVF) 22 relatively spatially registering the planning image 16 and the treatment image 14. The DVF 22 is also known in the art by other, similar nomenclature, such as the displacement field, and the term deformation vector field or DVF as used herein is intended to encompass these various nomenclatures. The DVF 22 relatively spatially registers the planning and treatment images by specifying for pixels or voxels of one image the displacement transformation (including both distance and direction) in order to align with the second image. The DVF 22 indicates the displacement transformations to align the planning image with the treatment image, or indicates the displacement transformations to align the treatment image with the planning image. Non-rigid deformation (or non-rigid spatial registration, or similar phraseology) is obtained because the pixel or voxel displacement transformations can vary across the image to provide non-rigid deformation. The DVF 22 maps one image (e.g., the planning image) to the other image (e.g., the treatment image). However, it will be appreciated that mapping in the opposite direction (e.g., transforming the treatment image to align with the planning image) can also be performed using the DVF 22 by suitable reversal of the pixel or voxel vector transformations. Thus, generally speaking the DVF 22 spatially maps a first image (e.g., the planning image 16) and a second image (e.g., the treatment image 14).

The DVF 22 can be used to update radiation therapy planning parameters. For example, the DVF 22 can be used to warp the dosage, and/or to warp the attenuation map, in order to account for changes such as movement, shrinkage, or expansion of the tumor and/or various critical organs.

Additionally, the DVF 22 can be used to adjust planning image contours 26 associated with the planning image 16. (For example, the planning image 16 along with the contours 26 and other metadata such as acquisition time, imaging parameters, and so forth may be stored in a file 28 denoted diagrammatically in FIG. 1 by a dotted box surrounding the components 16, 26.) In some suitable embodiments, the contours 26 are generated by the oncologist by manually delineating the contours 26. Optionally, the contouring of the planning image 16 may be assisted by an automated contouring algorithm (e.g., semi-automated contouring).

Contouring is generally difficult, because the boundaries different soft-tissue organs can be difficult to detect by a trained human observer or by an automated segmentation algorithm. The difficulty is enhanced by poor soft-tissue contrast in CT scans. During the initial radiation therapy planning, the oncologist or other medical personnel perform the tedious task of contouring the tumor and critical structures in the planning image. It is preferable to avoid repeating such tedium each time a new treatment image is acquired to track changes in the patient.

One approach for simplifying the contouring of the treatment image 14 is to use the planning contours 26 as patient-specific priors, and to use the DVF 22 to map the planning image contours 26 from the planning image 16 to the treatment image 14. This approach is known in the art as region of interest (ROI) warping or propagation. The warped contours provide automatic delineation of the target tumor and critical structures in the treatment image 14, without performing tedious manual contouring.

However, this approach introduces a substantial risk, in that any mapping error in the DVF 22 (which may be caused, for example, by severe deformation which is difficult to map accurately, or by image artifacts, or by features that appear in only one image, differences in contrast agent distribution between the planning and treatment images, or so forth). Any errors in the DVF 22 that are in the proximity of the contour undergoing mapping will be propagated into the warped contour. Since these contours are used for patient-critical operations such as defining radiation dose distributions that target the malignant tumor while substantially avoiding critical structures, any contour error can have substantial adverse consequences for the subject undergoing IMRT.

One way to address errors in the contour mapping is to allow the user (e.g., oncologist or radiologist) to view the contour superimposed on the treatment image 14 and, if errors are observed, to manually edit the contour using a mouse or other input device. However, this approach corrects only the contour, but not the DVF 22 that was the source of the erroneous contour. This can be a problem because some aspects of the radiation therapy, such as the attenuation map, dose accumulation map, and so forth, depend directly on the DVF 22 rather than on the contours.

In embodiments disclosed herein, improved user correction is provided by a contour/DVF correction module 30 which enables the user to correct contours and also propagates any such corrections back into the DVF 22 in order to create a corrected DVF 32. The adjusted or corrected DVF 32 (rather than the original DVF 22) is then input to a radiation therapy session preparation module 34 for use in operations such as dose warping performed by a dose warping sub-module 36, dose accumulation mapping performed by a dose accumulation tracking sub-module 38, or so forth. The resulting IMRT session plan is suitably executed by an IMRT delivery system 40, which may by way of illustrative example comprise a linear electron accelerator (LINAC), configured to perform tomographic irradiation, or a multi-beam radiation therapy apparatus, or so forth.

The electronic processing components 20, 30, 34 can be variously embodied by one or more electronic processing devices, such as an illustrative computer 42. The contour/DVF correction module 30 preferably includes user interfacing components such as an illustrative display device 44 and one or more user input devices such as an illustrative keyboard 46 and mouse 48. In other embodiments, a non-transitory storage medium stores instructions executable by an electronic processing device (such as the illustrative computer 42) to perform methods performed by the electronic processing components 20, 30, 34. Such a non-transitory storage medium may comprise, by way of illustrative example: a hard disk or other magnetic storage medium; an optical disk or other optical storage medium; an electrostatic memory such as a FLASH memory; a read-only memory (ROM); a random access memory (RAM); or so forth.

Figure 2:
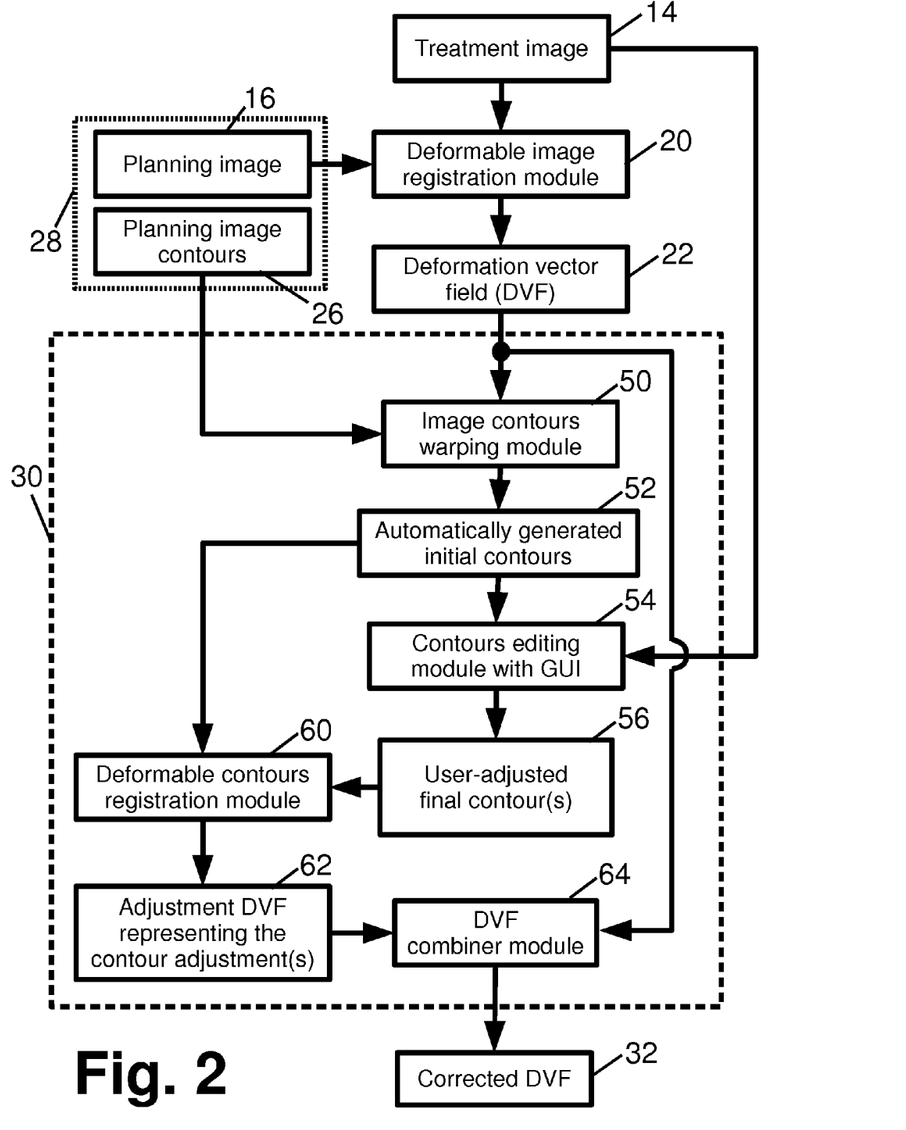
FIG. 2 diagrammatically shows the deformation vector field (DVF) correction module in additional detail.

With reference to FIG. 2, an illustrative embodiment of the contour/DVF correction module 30 is described. This module 30 receives as inputs: (1) the planning image contours 26; the DVF 22; and the treatment image 14. An image contours warping module 50 maps the planning image contours 26 to the treatment image 14 using the DVF 22 to automatically generate initial contours 52 for the treatment image 14. A contours editing module 54, which includes a graphical user interface (GUI), displays the treatment image 14 and an overlaid contour comprising the initial contour 52.

Figure 3:
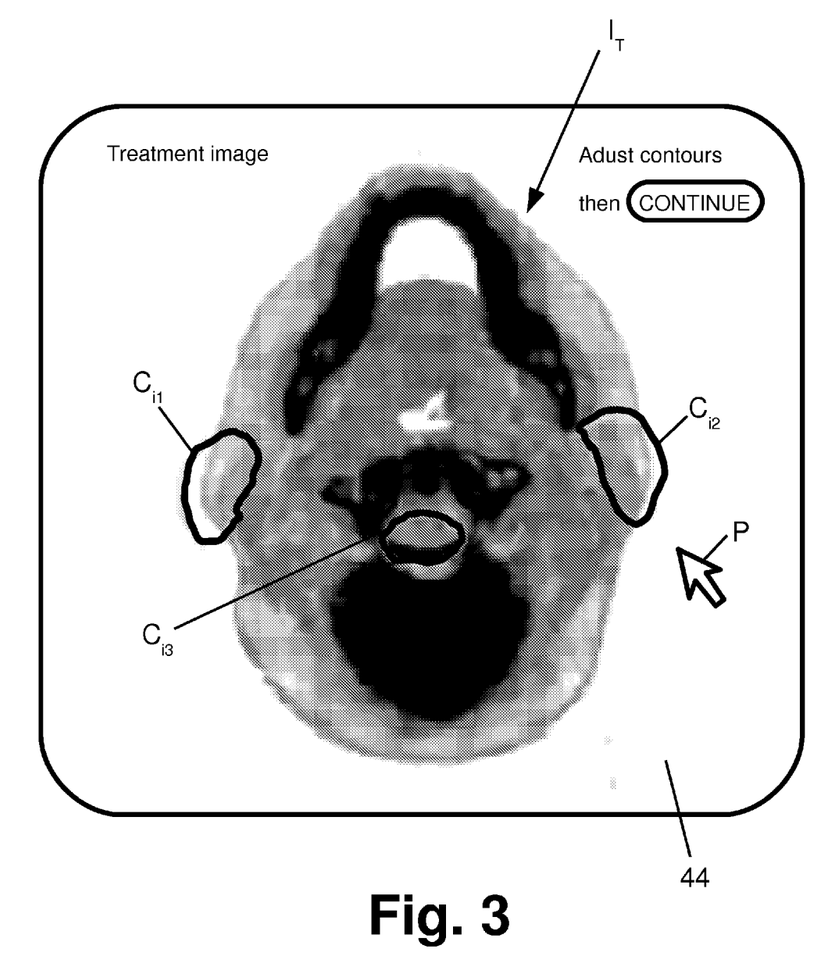
FIGS. 3-4 diagrammatically show a user interface display via which a user may input contour adjustments.

With brief reference to FIG. 3, these aspects are illustrated by a diagrammatic example. FIG. 3 shows a treatment image $I_T$ (corresponding to the treatment image 14 of FIGS. 1 and 2) displayed on the display device 44, along with initial contours $C_{i1}$, $C_{i2}$, $C_{i3}$ corresponding to the automatically generated initial contours 52 of FIG. 2 shown as overlaid contours that are overlaid on the treatment image $I_T$ displayed on the display device 44. The contours editing module 54 also provides instructions to the user for editing the contours $C_{i1}$, $C_{i2}$, $C_{i3}$, e.g. the displayed text "Adjust contours then (CONTINUE)". It is noted that the contours $C_{i1}$, $C_{i2}$, $C_{i3}$, are close to, but not precisely aligned with, apparent image features. The misalignment is due to some errors in the DVF 22 used to map the planning image contours to the treatment image 14.

Figure 4:
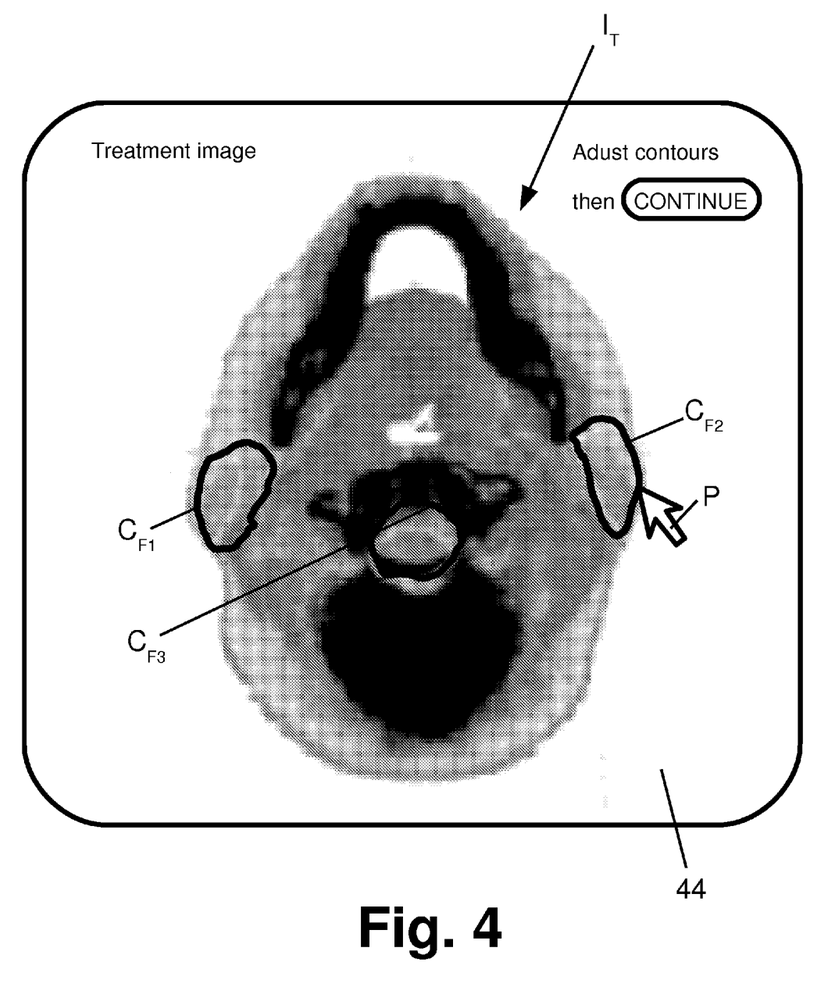

With continuing reference to FIGS. 2 and 3 and with further reference to FIG. 4, the user suitably uses an on-screen pointer P controlled by the mouse 48 (or by a trackball or other pointing-type user input device) to adjust the initial contours $C_{i1}$, $C_{i2}$, $C_{i3}$ by making various user adjustments to create final contours $C_{F1}$, $C_{F2}$, $C_{F3}$ shown in FIG. 4. For example, a "select, drag-and-drop" process can be used, in which the user points to a portion of a contour, clicks and holds a mouse button to select that portion, drags it to a new position, and releases the mouse button to "drop" the contour portion into its new location. Optionally, the process can be repeated to make a plurality of user adjustments, and in some embodiments the overlaid contours shown on the display device 44 are updated after each such user adjustment to reflect the updated contour. As per the instructions on the screen, once the user is satisfied with the adjusted contours, he or she clicks the "(CONTINUE)" button.

With reference back to FIG. 2, the final $C_{F1}$, $C_{F2}$, $C_{F3}$ shown in FIG. 4 constitute user-adjusted final contours 56 in FIG. 2. These final contours 56 are corrected for errors in the DVF 22; however, the DVF 22 does not itself include the user adjustments embodied in the final contours 56.

To propagate these adjustments back into the deformation vector field, a deformable contours registration module 60 receives the initial contours 52 and the final contours 56, and computes an adjustment deformation vector field (adjustment DVF) 62 that accounts for the user adjustments. The deformable contours registration module 60 uses a deformable image registration algorithm such as the Demons deformable registration technique or another deformable image registration technique such as level sets, B-spline, or so forth to generate the adjustment DVF 62 that maps the initial contour 52 to the final contour 56 (or vice versa). A DVF combiner module 64 combines the DVF 22 (which does not have correction) and the adjustment DVF 62 to generate the corrected DVF 32. The superposition rule applies to this combining operation, and accordingly the combiner module 64 suitably operates by adding the adjustment DVF 62 to the DVF 22 to generate the corrected DVF 32. This addition operation assumes that both the DVF 22 and the adjustment DVF 62 have the same "sign", i.e. map in the same direction (e.g., mapping the planning image to the treatment image and the initial contour to the final contour). If the DVF 22 and the adjustment DVF 62 have opposite "sign" (e.g., the DVF 22 maps the planning image to the treatment image while the adjustment DVF 62 maps the final contour to the initial contour), then the combiner module 64 suitably operates by subtracting the adjustment DVF 62 from the DVF 22 to generate the corrected DVF 32.

Figure 5:
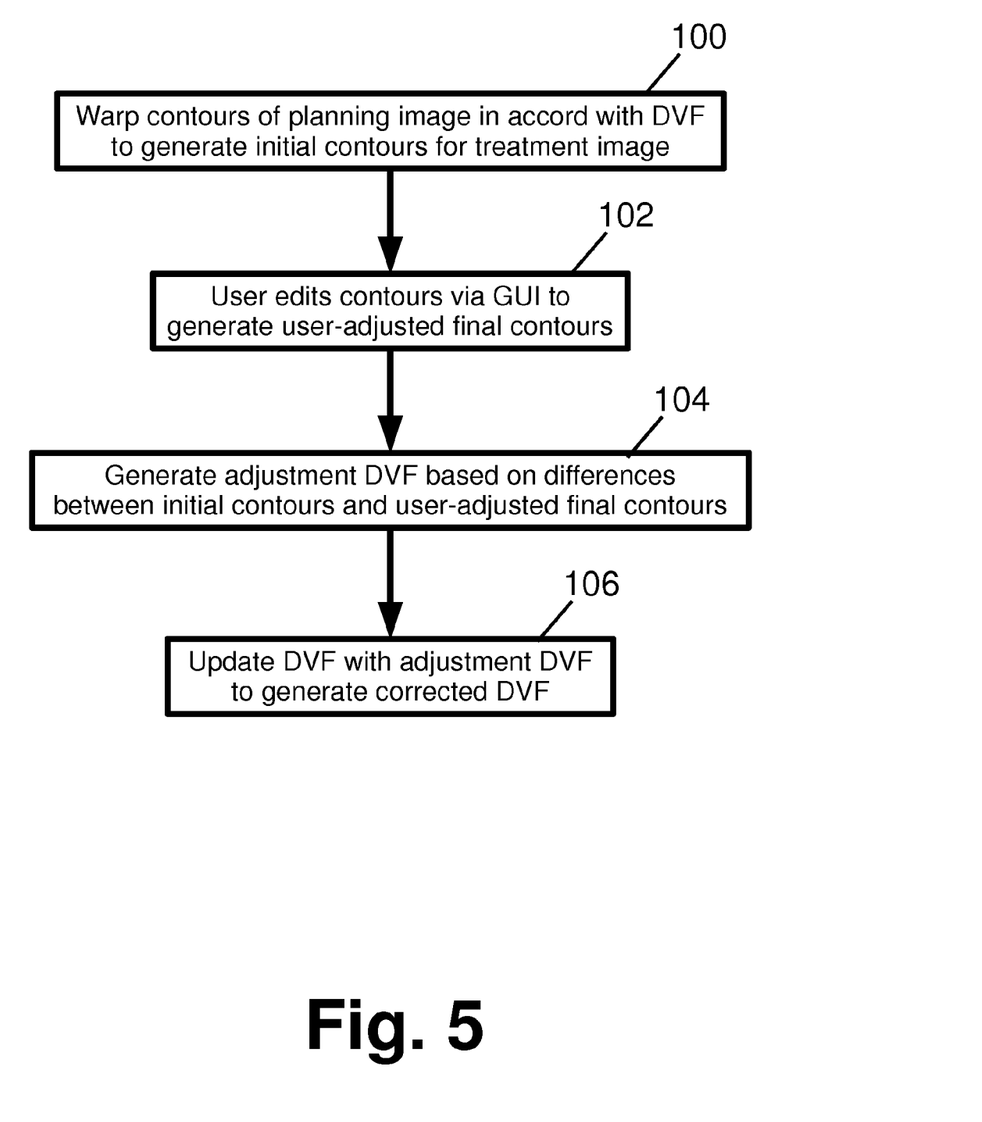
FIG. 5 diagrammatically shows a process suitably performed by the contour/DVF correction module of FIG. 2.

With continuing reference to FIG. 2 and with further reference to FIG. 5, a process suitably performed by the contour/DVF correction module 30 is described. In an operation 100 performed by the image contours warping module 50, the contours 26 of the planning image 16 are warped in accordance with the DVF 22 to automatically generate the initial contours 52. In an operation 102, a user employs a graphical user interface (GUI) to edit the initial contours 52 in order to generate user-adjusted final contours 56. In an operation 104 performed by the deformable contours registration module 60, the adjustment DVF 62 is generated based on differences between the initial contours 52 and the final contours 56. In an operation 106 performed by the DVF combiner module 64, the DVF 22 is updated with the adjustment DVF 62 to generate the corrected DVF 32.

In the illustrative embodiments, the final contour 56 delineating the structure in the treatment image 14 is generated by user adjustment of the initial contour 52. In an alternative embodiment, the final contour may be generated by performing an automated optimization of the mapped initial contour 52 respective to the structure in the treatment image 14 to generate the final second image contour delineating the structure in the treatment image. Moreover, while the contour/DVF adjustment has been disclosed herein in the context of IMRT, the contour/DVF adjustment is suitably applied to other applications in which a first image (e.g., the planning image 16 in the illustrative embodiment) is contoured to generate first image contours (e.g., contours 26 in the illustrative embodiment), a second image is acquired (e.g., the treatment image 14 in the illustrative embodiment), and non-rigid image registration is applied to generate a DVF mapping between the first and second images. For example, the first image may be a reference image acquired of a laboratory test animal prior to commencement of a pre-clinical test, and the second image may be subsequent images of the laboratory test animal acquired at various points during the pre-clinical test. As another example, the first image may be a reference image acquired of a human subject prior to commencement of a clinical trial, and the second image may be subsequent images of the human subject acquired at various points during the clinical trial. Other contemplated applications include various radiation therapy techniques such as IMRT and specific techniques such as conformal arc therapy or volumetric-modulated arc therapy (VMAT), various pre-operative surgical planning procedures, interventional imaging or image guided surgery, post-operative assessment, and so forth, each of which readily benefit from contour/DVF adjustment as disclosed herein.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A method comprising:
    computing a deformation vector field (DVF) relatively spatially registering first and second images;
    adapting a contour delineating a structure in the first image using the DVF to generate an initial contour for the structure in the second image;
    receiving a final contour for the structure in the second image; and
    correcting the DVF based on the initial and final contours for the structure in the second image to generate a corrected DVF;
    wherein the computing, adapting, and correcting are performed by an electronic processing device; and
    wherein the correcting comprises:
    computing an adjustment deformation vector field (adjustment DVF) relating the initial and final contours for the structure in the second image;
    and combining the DVF and the adjustment DVF to generate the corrected DVF.

2. The method of claim 1, wherein the combining comprises one of:
    adding the adjustment DVF to the DVF to generate the corrected DVF, and
    subtracting the adjustment DVF from the DVF to generate the corrected DVF.

3. The method of claim 1, wherein the receiving comprises:
    displaying the second image and an overlaid contour comprising the initial contour for the structure in the second image; and
    receiving one or more user adjustments of the overlaid contour, the displaying of the overlaid contour being updated responsive to each received user adjustment;
    wherein the final contour for the structure in the second image comprises the initial contour including the received one or more user adjustments.

4. The method of claim 1, wherein the first image is a planning image for generating a radiation therapy plan and the second image is a treatment image for updating the radiation therapy plan, and the method further comprises:

updating one or more parameters of the radiation therapy plan to account for change occurring between acquisition of the planning image and acquisition of the treatment image, the updating being based at least on the corrected DVF.

5. The method of claim 4, wherein the updating of one or more parameters of the radiation therapy plan includes updating at least one of: (1) an attenuation map, (2) a dose warping, and (3) a dose accumulation.

6. The method of claim 4, further comprising:

performing a radiation therapy session using the one or more updated parameters.

7. A non-transitory storage medium storing instructions executable by an electronic processing device to perform a method as set forth in claim 1.

8. An electronic processing device configured to perform a method as set forth in claim 1.

9. A non-transitory storage medium storing instructions executable by an electronic processing device to perform a method comprising:

adjusting a contour of a second image;

updating a deformation vector field (DVF) mapping between the second image and a first image based on the adjustment of the contour to generate an updated DVF mapping between the second image and the first image; and wherein the updating comprises:

computing an adjustment DVF representing the adjustment of the contour; and combining the DVF and the adjustment DVF to generate the updated DVF.

10. The non-transitory storage medium as set forth in claim 9, wherein the method further comprises:

prior to the adjusting, generating the contour of the second image by applying the DVF to a contour of the first image.

11. The non-transitory storage medium as set forth in claim 9, wherein the adjusting comprises:

displaying the second image and the contour of the second image overlaid on the displayed second image; and receiving and displaying user adjustments of the displayed overlaid contour.

12. The non-transitory storage medium as set forth in claim 9, further comprising:

generating the deformation vector field (DVF) by relatively spatially registering the first and second images.

13. The non-transitory storage medium as set forth in claim 9, wherein the first image is a planning image for generating a radiation therapy plan and the second image is a treatment image for updating the radiation therapy plan, and the method further comprises:

updating one or more parameters of the radiation therapy plan to account for change occurring between acquisition of the planning image and acquisition of the treatment image, the updating being based at least on the adjusted DVF.

14. An apparatus comprising:

an electronic processing device configured to compute a deformation vector field (DVF) spatially mapping a first image and a second image; and a user interface configured to display the second image and an overlaid contour comprising an initial contour generated by mapping a contour of the first image to the second image using the DVF, the user interface further configured to receive and display user adjustments of the overlaid contour wherein the overlaid contour adjusted by said user adjustments defines a final contour;

the electronic processing device further configured to correct the DVF based on the initial contour and the final contour to generate a corrected DVF;

wherein the electronic processing device is configured to correct the DVF by:

computing an adjustment DVF spatially mapping the initial contour and the final contour; and combining the DVF and the adjustment DVF to generate the corrected DVF.

15. The apparatus of claim 14, wherein the first image is a planning image for generating a radiation therapy plan and the second image is a treatment image for updating the radiation therapy plan, and the electronic processing device is further configured to update one or more parameters of the radiation therapy plan based at least on the corrected DVF.

16. The apparatus of claim 15, wherein the updating of one or more parameters of the radiation therapy plan is further based on the treatment image.

17. The apparatus of claim 15, further comprising:

a radiation therapy delivery system configured to perform a radiation therapy session using the one or more updated parameters.

* * * * *